United States Patent
Ramakrishna et al.

(10) Patent No.: US 6,383,495 B1
(45) Date of Patent: *May 7, 2002

(54) HERBAL FORMULATION USEFUL FOR TREATMENT OF SKIN DISORDERS

(75) Inventors: Sistla Ramakrishna; Bhamidipalli Subrahmanya Sitaramam; Prakash Vaman Rao Diwan; Kondapuram Vijaya Raghavan, all of New Delhi (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

This patent is subject to a terminal disclaimer.

(21) Appl. No.: 09/659,124

(22) Filed: Sep. 11, 2000

Related U.S. Application Data

(63) Continuation-in-part of application No. 09/199,588, filed on Nov. 25, 1998, now Pat. No. 6,200,570.

(30) Foreign Application Priority Data

Dec. 8, 1997 (IN) ........................ 3519/DEL/97

(51) Int. Cl.⁷ .............................. A61K 35/78
(52) U.S. Cl. ............. 424/195.18; 424/725; 424/744; 424/764; 514/861; 514/886; 514/887
(58) Field of Search .................. 424/764, 725, 424/744, 195.18; 514/861, 886, 887

(56) References Cited

U.S. PATENT DOCUMENTS

| 5,232,769 A | * | 8/1993 | Yamato et al. |
| 5,618,544 A | * | 4/1997 | Brown |
| 5,834,513 A | * | 11/1998 | Ptchelintsev et al. |
| 5,958,418 A | * | 9/1999 | Prillerman |
| 6,010,701 A | * | 1/2000 | Matsukura et al. |

FOREIGN PATENT DOCUMENTS

| HU | 50622 | * | 3/1990 |
| HU | 50623 | * | 3/1990 |
| WO | 9833494 | | 8/1998 |

OTHER PUBLICATIONS

Sundarraj et al. Indian Phytophatol. vol. 49(4), pp. 398–403, Abstract Enclosed, 1996.
Product Alert Bulletin of Jul. 22, 1996—Abra Therapeutic Lotion.
Castleman, M. The Healing Herbs, Rodale Press, Emmaus, Pennsylvania, pp. 42–44, 1991.*

* cited by examiner

Primary Examiner—Christopher R. Tate
(74) Attorney, Agent, or Firm—Rankin, Hill, Porter & Clark LLP

(57) ABSTRACT

The invention provides a novel herbal formulation useful for the treatment of skin disorders and comprising two or more plant extracts selected from *Tagetes erecta, Moringa oleifera, Ocimum sanctum, Tridax procumbens, Aloe vera*, and *Gum olibanum* together with conventional additives.

17 Claims, No Drawings

HERBAL FORMULATION USEFUL FOR TREATMENT OF SKIN DISORDERS

CROSS-REFERENCE TO RELATED APPLICATIONS

This application is a continuation-in-part of U.S. application Ser. No. 09/199,588 filed Nov. 25, 1998, now U.S. Pat. No. 6,200,570.

FIELD OF THE INVENTION

The present invention relates to a herbal formulation useful for treatment of skin disorders like dry eczema and corns on the feet and for alleviating muscular pain due to exertion. The herbs that are used in this invention are known to possess activity against eczema and corn and they also possess analgesic property.

BACKGROUND AND PRIOR ART OF THE INVENTION

Eczema is a generic term for acute or chronic inflammatory condition of the skin, typically erythematous, edematous, papular, vascular and crusting followed by lichenification and scaling and occasionally by duskiness of erythema infrequently by hyper pigmentation, often accompanied by sensation of itching and burning. It is also called as dry tetter.

Dermatitis is eczematous unless specifically stated to the contrary. The earliest sign of eczema is erythema, occasioned by dilatation of dermal blood vessels, and this persists to a greater or lesser degree until healing takes place. The next stage consists of invasion of epidermis by lymphocytes and an increase in its cellular and intercellular fluid. The latter collects in to minute vesicles. The vesicles soon rupture, leading to exudation of serum onto the surface, which after some time dry up and form crusts. As a result of these changes, the normal function of epidermis is interfered with. It: fails to form healthy horn cells, the surface of the skin becoming scaly (parakeratosis). Also, the cellular division may be increased leading to general thickening of the epidermis which when extreme, results in "lichenification".

Corns referred to as hyperkeratosis, result from friction and pressure, and the skin responds by becoming thicker and tougher as a protective mechanism. The horny, outer layer of the skin called the "stratum corneum" becomes thicker in the area where there is an increased pressure or rubbing. A corn has a hard core, a bit like an upside down pyramid, with the base at the surface of the skin, and the point pushing inward. When this point presses against the nerve endings in the nearby tissue, a stabbing pain may the result. The treatment of corns begins by attacking the cause, preventing the friction and relieving the pressure on the area. Specially medicated plasters containing chemicals that can dissolve the tissue (keratolytics.).

Treatment of eczema consists use: of corticosteroids such as hydrocortisone and other steroidal anti-inflammatory drugs. Drugs like Betamethasone valerate and Clobetasone propionate were used topically as creams containing betamethasone valerate 0.12% and clobetasone 0.05%.

For treating corns, presently, "corn caps" are available in the market (manufactured) by Indoteck Laboratories, Rohtak, India) a corn dressing which contains salicylic acid—30%, Benzoic acid—10% and *Saraca indica*—10% w/w. The ingredients have keratolytic property. The disadvantages with the presently available commercial product are that different sizes of caps are necessary depending on the size of the corn on the toes. The corn caps should not be used in cuts and burns. Also, the preparation is contraindicated in diabetic patients.

Accordingly, studies were undertaken to develop cream formulations containing herbal drugs and synthetic ingredients for topical application over the affected areas which will help in alleviating muscular pain due to exertion and for reducing itching and burning sensation in cases of eczema and reducing the pain in places where corns are present.

OBJECTS OF THE INVENTION

The main object of the present invention is to provide a novel herbal formulation useful for treatment of skin disorders and alleviating muscular pain.

Another object is to provide a formulation useful for the treatment of eczema and corn.

Yet another object of the present invention is to provide a method for the treatment of skin disorders and muscular pain using the formulation of the invention.

SUMMARY OF THE INVENTION

Accordingly, the invention provides a novel herbal formulation useful for the treatment of skin disorders and comprising two or more plant extracts selected from *Tagetes erecta, Moringa oleifera, Ocimum sanctum, Tridax procumbens, Aloe vera,* and *Gum olibanum* together with conventional additives.

DETAILED DESCRIPTION OF THE INVENTION

Accordingly, the present invention provides a novel herbal formulation useful for alleviating muscular pains and for treating skin disorders such as eczema and corns, said formulation comprising:

a) two or more plant extracts in the form of oil or extracts or powder or mixtures thereof, the plants extracts being selected from the group comprising *Tagetes erecta* 1 to 5 wt. %, *Moringa oleifera* 2 to 4 wt. %, *Ocimum sanctum* 0.3 to 3 wt. %, *Tridax procumbens* 2 to 6.5 wt. %, dried juice of *Aloe vera* 2 to 6.5 wt. %, *Gum olibanum* powder in natural state 3 to 6 wt. %, and *Gum olibanuim* resinoid or organic extract 3 to 6 wt. %; and one or more of the following:

b) drugs having anti-inflammatory and wound healing property and present in the range of 0.02 to 5 wt %;

c) a base containing aqueous cream or gel in the range of 2 to 5 wt. %;

d) emulsifying ointment in the range of 26 to 42 wt. %;

e) one or more preservatives in the range of 0.1 to 0.2 wt. %;

f) a humectant 0.5 to 3%; and g) the balance being water or propylene glycol and water in the ratio of 50:50 to make 100 wt. %.

The novelty of the present investigation is (1) does not require high dosage of drugs like beta methasone valerate, clobetasone propionate and salicylic acid in the cases of eczematic conditions. (2) since the formulation is to be applied on the affected areas of the skin it obviates the need for different sizes of the corn caps which are available commercially. (3) unlike commercial formulations which act by counter irritant action for the relief of muscular pains, the present formulation acts increasing blood flow by dilating the blood vessels when applied on the affected skin areas.

In an embodiment, the plant extracts used may be *Tagetes Erecta, Moringa Oleifera, Ocimium Sanctum, Gum*

Olibanum, *Tridax Procumbens*, Sandal wood, *Aloe Vera* from any part of the plant such as leaf, root, bark, natural exudation of the bark, flower, fruit, stem or branch.

In still another embodiment, the base used may be such as aqueous cream base (containing emulsifying ointment BP 1993, preservative and water) or gel base (containing propylene glycol, carbopol 934 and mondethanol amine).

In yet another embodiment, the preservatives used may be such as Methyl paraben, Propyl paraben, p-Chlorocresol.

In still another embodiment, the humectants used may be as Glycerine.

In an embodiment, the extract of *Tagetes erecia* is a water extract.

In still another embodiment, the extract of *Moringa oleifera* is a leaf extract.

In yet another embodiment, the extract of *Ocimum sanctum* is a steam distilled oil extract.

In another embodiment, humectant is glycerine and present in the range of 0.5 to 3 wt. %, In an embodiment, the anti-inflammatory drugs are selected from Beta methasone valerate present in the range of 0.03 to 0.09 wt. %, Clobetasone propionate present in the range of 0.03 to 0.08 wt. %, Salicylic acid present in the range of 1 to 3 wt. % and Sandal wood oil in the range of 0.3 to 0.8 wt. %.

In yet another embodiment, *Gum olibanum* resinoid hexane extract ranges between 3 to 6wt. %.

In still another embodiment, the *Gum olibanum* organic extract is a *Gum olibanum* methanolic extract and ranges between 3 to 6 wt. %.

In another embodiment, the gel is a base containing propylene glycol, carbopol 934 and monoethanolamine.

In an embodiment, the base is an aqueous cream containing emulsifying ointment BP1993.

In another embodiment, the skin disorders are selected from the group consisting of Eczema and corns.

In still another embodiment, the formulation is used as anti-inflammatory agent and wound healing agent.

In another embodiment, the formulation is in the form of an emulsion of cream for application to the skin.

The invention also provides a method for the treatment of Eczema comprising the steps of application of the herbal formulation, to a subject in need thereof at least two times a day for a period of 90–120 days.

In an embodiment, the herbal formulation of the invention is applied at least two times a day for a period of 60–90 days for the treatment of Corn.

In yet another embodiment, the herbal formulation of the invention is applied at least two times a day for a period of at least two days for alleviating muscular pains.

As a result of intensive study conducted by the inventors with the aim of achieving aforementioned objectives, new processes for the preparation of cream formulations for topical use were developed employing herbal drugs which are from natural origin, incorporating them into cream bases along with synthetic materials which are known to possess water retaining properties.

Accordingly, the present investigation deals with cream and gel based topical formulations. Each formulation has been described in detail giving the formula of the ingredients along with method of preparation.

The first step in the preparation of these formulations involves a process for making the plant material suitable for incorporating into cream/gel bases. The specified portion of the plant is collected and dried under shade at room temperature in an enclosed room for 72 hrs or more until the material gets dried. A specified amount of material is then extracted with solvents like n-hexane, chloroform, ethanol, methanol and water, in cold condition. The choice of the solvent depends upon the type of material expected at the end of extraction process. Extraction process was carried out in a closed container immersing specified amount of the plant material in respective solvents for 72 hrs. At the end of this stage, solvent is decanted and filtered if necessary to make it free from the plant debris. The solvent is then concentrated by evaporating under vacuum at room temperature. If the solvent used is water, then concentrated solution is freeze dried to obtain the final product in, powder form. If the solvent used is a non-polar solvent then final product would be an oily and viscous substance with specific physico-chemical properties. This final product is made into a formulation intended for topical use by using it as an ingredient for making creams and gels. Suitable preservatives like methyl paraben, propyl paraben and p-chlorocresol have been used. Humectants such as propylene glycol and glycerol have been used in appropriate quantities.

Note:

The following are to be noted while making these formulations.

1. All the ingredients are expressed in % w/w basis.
2. Emulsifying ointment used in these formulations is prepared as per the procedure given in the official compendium (British Pharmacopoeia, 1993).
3. Carbopol 934 is a trade name given by the manufacturer. The generic name is Carbomer 934. It is a high molecular weight polymer of acrylic acid cross-linked with allyl ethers of sucrose. Carbomer 934, previously dried in vacuum at 80° for 1 hour, contains not less than 56.0 percent and not more than 68.0 percent of carboxylic acid (—COOH) groups. The viscosity of neutralized 0.5 percent aqueous dispersion of Carbomer 934 is between 30,500 and 39,400 centipoise. Reference: United States Pharmacopeia/The National Formulary, USP 23/NF 18, 1995, United States Pharmacopeial Convention, Inc. 12601, Twinbrook, Parkway, Rockville, Md. 20852. Page 2226.

The following examples have been given by way of illustration and therefore should not be construed to limit the scope of the present invention.

Formulations for alleviating muscular pain.

EXAMPLE-1

| | |
|---|---|
| *Gum olibanum* resinoid (n-Hexane extract) | 3–6% |
| *Tridax procumbens* leaf extract | 3–6% |
| *Tagetes Erecta* leaf extract | 1–3.5% |
| Emulsifying ointment | 33–42% |
| Methyl paraben | 0.1–0.2% |
| Propyl paraben | 0.1–0.2% |
| Purified Water | q.s. 100% |

Procedure: *Gum Olibanum* lumps were powdered in 5 Kg lots in an edge runner mill for 30 minutes. The powdered raw *Gum Olibanum* (250 gms) was then extracted at 30° C. using n-hexane (1.5 liters) as solvent in a vertical churner for 8 hrs. The solvent containing resinoid was then decanted and was distilled off at atmospheric pressure. The resinoid (100 gms) was obtained which is pale yellow and having a refractive index of 1.5160, density 0.9287 gms/cc and surface tension 0.0290 N/M at 30° C.

The leaves of *Tridax Procumbens* were shade dried for 48 hrs at room temperature. The crushed leaves (500 gms) were then soaked with water (1 liter) for 72 hrs at room temperature. At the end of this period, water is decanted and then concentrated to 100 ml by evaporating under vacuum at room temperature. This concentrated solution is then lyophilized to obtain powder.

The tender leaves of *Tagetes Erecta* were shade dried for 48 hrs at ambient temperature. The leaves (500 gms) were soaked with water (1 lt.) for 72 hrs at room temperature. As end of this period, water is decanted and then concentrated to 100 ml by evaporating under vacuum at room temperature. This concentrated solution is then lyophilized to obtain powder.

Weighed quantity of emulsifying ointment is taken in a tared vessel along with gum olibanum resinoid and propyl paraben and heated until the ointment melts. In a separate container, *Tridax Procumbens* leaf extract and *Tagetes Erecta* leaf extract were dispersed in water. Required quantity of methyl paraben is also added. This aqueous mixture is heated to the same temperature as that of emulsifying ointment. The aqueous phase is then added to the oily phase, in hot condition and the mixture is stirred at 10,000 rpm for 1–3 hrs until a cream consistency is obtained.

This formulation is useful for alleviating muscular pains due to exertion.

EXAMPLE-2

| | |
|---|---|
| Gum olibanum powder | 3–6% |
| *Tridax procumbens* leaf extract | 3–6% |
| *Aloe vera* | 3–6.5% |
| *Tagetes erecta* leaf extract | 1.5–4.5% |
| Emulsifying ointment | 28–37% |
| P-chlorocresol | 0.1–0.2% |
| Purified water | q.s 100% |

Procedure: The naturally occurring *Gum Olibanum* exudate in dry state is taken as it is. The lumps (1 kg) were powdered in an edge runner for 30 minutes. The powdered raw gum was passed through 100-mesh screen.

The leaves of *Tridax Procumbens* were shade dried for 48 hrs at room temperature. The crushed leaves (500 gms) were then soaked with water (1 liter) for 72 hrs at room temperature. At the end of this period, water is decanted and then concentrated to 100 ml by evaporating under vacuum at room temperature. This concentrated solution is then lyophilised to obtain powder.

The tender leaves of *Tagetes Erecta* were shade dried for 48 hrs at ambient temperature. The leaves (500 gms) were soaked with water (1 lt.) for 72 hrs at room temperature. As end of this period, water is decanted and then concentrated to 100 ml by evaporating under vacuum at room temperature. This concentrated solution is then lyophilized to obtain powder.

Weight quantities of p-chlorocresol and emulsifying ointment are taken in container and mixture heated until both the mixture melts (oil phase). *Gum Olibanum* powder, *Tridax Procumbens* leaf extract, dried juice of *Aloe Vera* and water extract of *Tagetes Erecta* are dispersed in water in a suitable container and mixture is kept for homogenization until a homogenous dispersion is obtained. This dispersion (aqueous phase) is heated for the same temperature as that of oil phase. The aqueous dispersion is added to the oil phase containing resinoid and emulsifying ointment in hot condition while under stirring for 1 hr at 10,000 rpm until a cream consistency is obtained.

This formulation is useful for alleviating muscular pains and also acts as skin conditioner.

EXAMPLE-3

| | |
|---|---|
| *Tridax procumbens* leaf extract | 3–6% |
| *Tagetes erecta* leaf extract | 2–5% |
| Carbopol 934 | 2–4% |
| Methyl paraben | 0.1–0.2% |
| Propyl paraben | 0.1–0.2% |
| Monoethanol amine | q.s. to get pH 6.0 |
| Propylene glycol:water (50:50) | q.s. to 100% |

Procedure: The leaves of *Tridax Procumbens* were shade dried for 48 hrs at room temperature. The crushed leaves were then soaked with water for 72 hrs at room temperature. At the end of this period water is decanted and then concentrated to 100 ml by evaporating under vacuum. This concentrated solution is then lyophilized to obtain a powder.

The tender leaves of *Tagetes Erecta* were shade dried for 48 hrs at ambient temperature. The leaves (500 gms) were soaked with water (1 lt.) for 72 hrs at room temperature. As end of this period, water is decanted and then concentrated to 100 ml by evaporating under vacuum at room temperature. This concentrated solution is then lyophilized to obtain powder.

The dried leaf extracts of *Tridax Procumbens* and *Tagetes Erecta* and propyl paraben were dissolved in pure propylene glycol by vigorous mixing using a mechanical stirrer. Carbopol 934 was dispersed separately in propylene glycol and water mixture (50:50) along with methly paraben in another vessel. The mixture is stirred continuously for 1–3 hrs at 300 rpm using mechanical stirrer or homogenizer. The pure propylene glycol solution containing *tridax procumbens, tagetes erecta* and propyl paraben was then added to the previous mixture. Stirring was continued for 1 hr until a gel preparation was obtained. The pH of the gel is adjusted to 6.0 using monoethanolamine. The final gel preparation will be clear, transparent and non-sticky.

This gel preparation is useful for reducing muscular pains due to exertion.

EXAMPLE-4

| | |
|---|---|
| Gum oilibanum (Raw) powder | 4–6% |
| *Tridax procumbens* leaf extract | 4–6% |
| *Tagetes erecta* leaf extract | 2–4% |
| Tulsi (*ocimum sanctum*) oil | 0.5–3% |
| *Aloe vera* dried juice | 3–6% |
| Glycerine | 1–3% |
| P-chlorocresol | 0.1–0.2% |
| Emulsifying ointment | 28–36% |
| Purified water | q.s to 100% |

Procedure: The naturally occurring *Gum Olibanum* exudate in dry state is taken as it is. The lumps (1 kg) were powdered in an edge runner for 30 minutes. The powdered raw gum was passed through 100 mesh screen.

The leaves of *Tridax Procumbens* were dried under shade at room temperature for 72 hrs. The leaves were crushed to powder and the powder (500 gm) was soaked with water (1 lt) for a week. Water is then decanted, filtered and concentrated to 100 ml. The concentrated solution was then lyophilized to get powder.

The tender leaves of *Tagetes Erecta* were shade dried for 48 hrs at ambient temperature. The leaves (500 gms) were soaked with water (1 lt.) for 72 hrs at room temperature. As end of this period, water is decanted and then concentrated to 100 ml by evaporating under vacuum at room temperature. This concentrated solution is then lyophilized to obtain powder.

The leaves of Tulsi (*Ocimum Sanctum*) were shade dried for 48 hrs and the dried leaves (1 Kg) were steam distilled to get the essential oil (yield 0.3 to 0.4%).

Weighed quantities of emulsifying ointment, dried juice of aloe vera, p-chlorocresol were taken in clean vessel cell and the mixture was melted while stirring to get a molten homogeneous mixture.

*Gum Olibanum* powder, dried powders of *Tridax Procumbens* and *Tagetes Erecta* and glycerin were dispersed in purified water using a mechanical stirrer. The temperature of this aqueous dispersion was brought to that of oil phase. The aqueous phase was then added to oil phase in hot condition, while stirring at 10,000 rpm using a homogenizer. Tulsi oil was added while the mass is congealing and stirring continued until the mass solidifies to clean consistency.

This formulation is useful for alleviating muscular pains. Apart from this it also acts as skin conditioner and moisturizer.

EXAMPLE-5

| | |
|---|---|
| *Tridax procumbens* leaf extract (Lyophilized) | 2–5% |
| *Aloe vera* | 2–6% |
| *Tagetes erecta* leaf extract | 2–4% |
| Carbopol 934 | 2–5% |
| Methyl paraben | 0.1–0.2% |
| Propyl paraben | 0.1–0.2% |
| Monoethanol amine | q.s. to get pH 6.0 |
| Propylene glycol:water (50:50) | q.s. to make 100% |

Procedure: The leaves of *Tridax Procumbens* were shade dried for 48 hrs at room temperature. The crushed leaves (500 gms) were then soaked with water (1 liter) for 72 hrs at room temperature. At the end of this period, water is decanted and then concentrated to 100 ml by evaporating under vacuum at room temperature. This concentrated solution is then lyophilized to obtain powder.

The tender leaves of *Tagetes Erecta* were shade dried for 48 hrs at ambient temperature. The leaves (500 gms) were soaked with water (1 lt.) for 72 hrs at room temperature. As end of this period, water is decanted and then concentrated to 100 ml by evaporating under vacuum at room temperature. This concentrated solution is then lyophilized to obtain powder.

The leaf extracts of *Tridax Procumbens* and *tagetes erecta* and dried juice of aloe vera along with propyl paraben were dissolved in pure propylene glycol by vigorous mixing using a mechanical stirrer. Carbopol 934 was dispersed separately in propylene glycol and water mixture (50:50) along with methyl paraben in another vessel. The mixture is stirred continuously for 1–3 hrs at 300 rpm using mechanical stirrer or homogenizer. The pure propylene glycol solution containing *Tridax Procumbens, Tagetes Erecta, Aloe Vera* and propyl praben was then added to the above mixture and stirring was continued until a gel preparation was obtained. The pH of this gel was adjusted to 6.0 using monoethanolamine. The final gel preparation will be clear, transparent and non-sticky.

This gel preparation is useful for alleviating muscular pains. It also acts as skin conditioner.

EXAMPLE-6

| | |
|---|---|
| *Tridax procumbens* leaf extract (Lyophilised) | 3–6% |
| *Gum Olibanum* powder | 3–6% |
| Tulsi oil (*Ocimum Sanctum*) | 0.3–0.8% |
| *Tagetes erecta* water extract | 1.5–4.5% |
| Betamethasone Valerate | 0.03–0.09% |
| Zinc salicylate | 1–3% |
| Aloe vera | 3–5% |
| p-Chlorocresol | 0.1–0.2% |
| Emulsifying ointment | 33–42% |
| Purified water | q.s. 100% |

Procedure: The naturally occurring *Gum Olibanum* exudate in dry state is taken as it is. The lumps (1 kg) were powdered in an edge runner for 30 minutes. The powdered raw gum was passed through 100-mesh screen.

The leaves of *Tridax Procumbens* were shade dried for 48 hrs at room temperature. The crushed leaves were then soaked with water for 72 hrs at room temperature. At the end of this period water is decanted and then concentrated to 100 ml by evaporating under vacuum. This concentrated solution is then lyophilized to obtain a powder.

The leaves of Tulsi (*Ocimum Sanctum*) were shade dried for 48 hrs and the dried leaves (1 Kg) were steam distilled to get the essential oil (yield 0.3 to 0.4%).

The tender leaves of *Tagetes Erecta* were shade dried for 48 hrs at ambient temperature. The leaves (500 gms) were soaked with water (1 lt.) for 72 hrs at room temperature. As end of this period, water is decanted and then concentrated to 100 ml by evaporating under vacuum at room temperature. This concentrated solution is then lyophilized to obtain powder.

Weighed quantities of Tulsi oil, Betamethasone valerate, p-chlorocresol and emulsifying ointment are taken in a tared container and mixture is heated until all ingredients melt. *Gum Olibanum* powder, *Tridax Procumbens* leaf extract powder, *Tagetes Erecta* leaf extract, zinc salicylate and dried juice of *Aloe Vera* are dispersed in water in a separate container and homogenized until a homogeneous dispersion is obtained. This aqueous dispersion is heated to the same temperature as that of molten oil phase containing emulsifying ointment and other ingredients. The aqueous phase is added to the oil phase while in hot condition and dispersed using a homogenize at 10,000 rpm for 2–3 hrs until cream consistency is obtained.

This formulation is useful for treating eczema of both acute and chronic type. It has keratolytic effect and aids in removing dead skin.

EXAMPLE-7

| | |
|---|---|
| *Gum olibanum* resinoid (MeOH extract) | 3–6% |
| *Tridax procumbens* leaf extract (Lyophilized) | 3–6% |
| *Tagetes erecta* leaf extract | 1–4% |
| Sandalwood oil | 0.3–0.8% |
| Methyl paraben | 0.1–0.2% |
| Propyl paraben | 0.1–0.2% |
| Emulsifying ointment | 32–38% |
| Purified water | q.s. to make 100% |

Procedure: *Gum Olibanum* lumps were powdered in 5 kg lots in an edge runner for 30 minutes. The powdered raw

*Gum Olibqum* (250 gm) was extracted at 30° C. using methyl alcohol (1.5 lt). The solvent containing resinoid was decanted and distilled off at atmospheric pressure to obtain the resinoid.

The leaves of *Tridax Procumbens* were shade dried for 48 hrs at room temperature. The crushed leaves were then soaked with water for 72 hrs at room temperature. At the end of this period water is decanted and then concentrated to 100 ml by evaporating under vacuum. This concentrated solution is then lyophilized to obtain a powder.

The tender leaves of *Tagetes Erecta* were shade dried for 48 hrs at ambient temperature. The leaves (500 gms) were soaked with water (1 lt.) for 72 hrs at room temperature. As end of this period, water is decanted and then concentrated to 100 ml by evaporating under vacuum at room temperature. This concentrated solution is then lyophilized to obtain powder.

Weighed quantities of *gum olibanum* resinoid, emulsifying ointment and propyl paraben were taken in clean container and heated under stirring until the mixture liquifies (oil phase). The dried leaf extracts of *Tridax Procumbens* and *Tagetes Erecta* along with methyl paraben were dispersed in purified water and the dispersion is heated to the same temperature as that of oil phase. The aqueous dispersion was then added to oil phase while stirring using a homogenizer at 10,000 rpm. Sandal wood oil is added when the mass is congealing. Stirring was continued until the mass solidifies and gives cream consistency.

This formulation is useful in alleviating muscular pains due to exertion.

EXAMPLE-8

| | |
|---|---|
| *Gum olibanum* powder | 3–6% |
| *Tridax procumbens* leaf extract | 3–6% |
| *Tagetes erecta* leaf extract | 1–3% |
| Betamethasone Valerate | 0.03–0.09% |
| Salicylic acid | 1–3% |
| Glycerene | 0.5–2% |
| p-Chlorocresol | 0.1–0.2% |
| Emulsifying ointment | 26–34% |
| Purified water | q.s. to make 100% |

Procedure: The naturally occurring *Gum Olibanum* exudate in dry state is taken as it is. The lumps (1 kg) were powdered in an edge runner for 30 minutes. The powdered raw gum was passed through 100 mesh screen.

The leaves of *Tridax Procumbens* were dried under shade at room temperature for 72 hrs. The leaves were crushed to powder and the powder (500 gm) was soaked with water (1 lt.) for a week. Water is then decanted, filtered and concentrated to 100 ml. The concentrated solution was then lyophilized to get powder.

The tender leaves of *Tagetes Erecta* were shade dried for 48 hrs at ambient temperature. The leaves (500 gms) were soaked with water (1 lt.) for 72 hrs at room temperature. As end of this period, water is decanted and then concentrated to 100 ml by evaporating under vacuum at room temperature. This concentrated solution is then lyophilized to obtain powder.

Weighed quantities of emulsifying ointment, betamethasone valerate and p-chlorocresol were taken in a clean vessel and mixture was melted while stirring to get a molten homogenous mixture (oil phase).

*Gum Olibanum* powder, the freeze dried extracts of *Tridax procumbens* and *Tagetes Erecta*, salicylic acid and glycerene were dispersed in purified water using mechanical stirrer. The temperature of this aqueous dispersion was brought to that of oil phase. The aqueous phase was then added to oil phase in hot condition, while stirring at 10,000 rpm using a homogenizer. The stirring was continued until the mass solidifies to cream consistency.

This formulation is useful for treating painful corns. It also softens the skin. It has keratolytic effect and removes dead skin.

EXAMPLE-9

| | |
|---|---|
| *Tridax procumbens* leaf extract (Lyophilized) | 3.5–6.5% |
| *Gum olibanum* powder | 4–6% |
| Tulsi (*Ocimum Sanctum*) oil | 0.3–0.8% |
| *Tagetes erecta* water extract | 2–5% |
| Clobetasone butyrate | 0.03–0.08% |
| Zinc salicylate | 1–2% |
| Aloe vera | 3–5% |
| p-chlorocresol | 0.1–0.2% |
| Emulsifying ointment | 30–38% |
| Purified water | q.s. to 100% |

Procedure: The leaves of *Tridax Procumbens* were dried under shade at room temperature for 72 hrs. The leaves were crushed to powder and the powder (500 gm) was soaked with water (1 lt) for a week. Water is then decanted, filtered and concentrated to 100 ml. The concentrated solution was then lyophilized to get powder.

The naturally occurring *Gum Olibanum* exudate in dry state is taken as it is. The lumps (1 kg) were powdered in an edge runner for 30 minutes. The powdered raw gum was passed through 100 mesh screen.

The tender leaves of *Tagetes Erecta* were shade dried for 48 hrs at ambient temperature. The leaves (500 gms) were soaked with water (1 lt.) for 72 hrs at room temperature. As end of this period, water is decanted and then concentrated to 100 ml by evaporating under vacuum at room temperature. This concentrated solution is then lyophilized to obtain powder.

The leaves of Tulsi (*Ocimum Sanctum*) were shade dried for 48 hrs and the dried leaves (1 Kg) were steam distilled to get the essential oil (yield 0.3 to 0.4%).

Weighed quantities of Tulsi oil, Cldbetasone butyrate, p-chlorocresol and Emulsifying ointment are taken in a tared container and the mixture is heated until all ingredients melt (oil phase). *Gum Olibanum* powder, *Tridax Procumbens* leaf extract powder, *Tagetes Erecta* leaf extract powder, Zinc salicylate and Dried juice of Aloe vera are dispersed in purified water in a separate container and stirred until a homogenous dispersion is obtained. This aqueous dispersion is heated to the same temperature as that of molten oil phase. The aqueous dispersion is added to the oil phase while in hot condition and dispersed using a homogenizer at 10,000 rpm for 2–3 hrs until cream consistency is obtained.

This formulation is useful for treating mild to moderate eczema.

EXAMPLE-10

| | |
|---|---|
| *Gum olibanum* powder | 3–6% |
| *Tridax procumbens* leaf extract | 3–6% |

| | |
|---|---|
| (Lyophilized) | |
| *Moringa Oleifera* leaf extract | 2–4% |
| Tulsi (*Ocimum sanctum*) oil | 0.3–0.8% |
| Betamethasone valerate | 0.03–0.09% |
| Zinc salicylate | 1–2% |
| Aloe vera | 3–5% |
| p-chlorocresol | 0.1–0.2% |
| Emulsifying ointment | 32–38% |
| Purified water | q.s. to 100% |

Procedure: The naturally occurring *Gum Olibanum* exudate in dry state is taken as it is. The lumps (1 kg) were powdered in an edge runner for 30 minutes. The powdered raw gum was passed through 100 mesh screen.

The leaves of *Tridax Procumbens* were dried under shade at room temperature for 72 hrs. The leaves were crushed to powder and the powder (500 gm) was soaked with water (1 lt) for a week. Water is then decanted, filtered and concentrated to 100 ml. The concentrated solution was then lyophilized to get powder.

The tender leaves of *Moringa Oleifera*, (Fam:Moringaceae) were shade dried for 48 hrs at ambient temperature. The leaves (500 gms) were soaked with water (1 lt.) for 72 hrs at room temperature. As end of this period, water is decanted and then concentrated to 100 ml by evaporating under vacuum at room temperature. This concentrated solution is then lyophilized to obtain powder.

The leaves of Tulsi (*Ocimum Sanctum*) were shade dried for 48 hrs and the dried leaves (1 Kg) were steam distilled to get the essential oil (yield 0.3 to 0.4%).

Weighed quantities of Tulsi oil, Betamethasone valarate, p-chlorocresol and Emulsifying ointment are taken in a tared container and the mixture is heated until all ingredients melt (oil phase). *Gum Olibanum* powder, *Tridax Procumbens* leaf extract powder, *Moringa Oleifera* leaf extract powder, Zinc salicylate and Dried juice of *Aloe Vera* are dispersed in purified water in a separate container and stirred until a homogenous dispersion is obtained. This aqueous dispersion is heated to the same temperature as that of molten oil phase. The aqueous dispersion is added to the oil phase while in hot condition and dispersed using a homogenizer at 10,000 rpm for 2–3 hrs until cream consistency is obtained.

This formulation is useful for treating eczema which is accompanied by itching and burning sensation. It also promotes removal of dead skin due to its keratolytic effect.

Case Studies for the Herbal Cream Formulations

| Parameters | Total No. of Patients | Number of Cured Patients | Results | Remarks |
|---|---|---|---|---|
| Corn | 12 | 12 | 60–90 days | Rough skin becomes smooth and healthy. No recurrence |
| Eczema | 6 | 6 | 90–120 days | Removes the hard skin and black color change to original skin color |
| Muscle pain | 20 | 20 | 1–2 days | Quick relief from the pain |

ADVANTAGES

The main advantages of the present inventions are:
1. The present formulations, apart from the therapeutic applications such as alleviating muscular pain due to exertion, are also useful in healing corns on toes and treating eczema.
2. The present formulations, which are used for alleviating muscular pains, do not contain any synthetic drugs compared to commercially available products in the market.
3. The present formulations have moisturizing effect on skin and hence can be used for dry skin disorders in cosmetic therapy.
4. The present formulations have keratolytic property and thus are useful in conditions of hyperkeratosis such as eczema and corns.
5. The present formulations provide excellent protection against corns and soften the hard skin, a common feature of corns. The present formulations meant for treating corns have the advantage that it can be used in diabetic conditions also, an advantage over commercially available "corn caps".
6. The present formulations can be used as base material in which ingredients having analgesic and anti-inflammatory property can be incorporated in low doses for potentiation of their activities.

What is claimed is:

1. An herbal formulation useful for alleviating muscular pain and for the treatment of skin disorders, said formulation comprising:
   a) two or more plant extracts in the form of an oil or powder or mixtures thereof, wherein a first of said plant extracts is *Tridax procumbens* water extract present in the range of 2 to 6.5 wt. % and a second of said plant extracts is selected from the group consisting of *Tagetes erecta* water extract present in the range of 1 to 5wt. %, *Moringa oleifera* water extract present in the range of 2 to 4 wt. %, *Ocimum sanctum* steam distilled oil extract present in the range of 0.3 to 3 wt. %, dried juice of *Aloe vera* present in the range of 2 to 6.5 wt. %, *Gum olibanum* powder in the dry natural form present in the range of 3 to 6 wt. %, and *Gum olibanum* resinoid organic solvent extract present in the range of 3 to 6 wt. %;

and one or more of the following:
   b) drugs having anti-inflammatory and wound healing properties present in the range of 0.02 to 5 wt. %;
   c) a base containing aqueous cream or gel present in the range of 2 to 5 wt. %;
   d) one or more emulsifiers present in the range of 26 to 42 wt. %;
   e) one or more preservatives present in the range of 0.1 to 0.2 wt. %;
   f) a humectant present in the range of 0.5 to 3%; and
   g) the balance being water or propylene glycol and water in the ratio of 50:50 to make 100 wt. %.

2. A formulation as claimed in claim 1 wherein the extract of *Moringa oleifera* is a leaf extract.

3. A formulation as claimed in claim 1 wherein the preservatives are selected from the group consisting of methyl paraben, propyl paraben and p-chlorocresol.

4. A formulation as claimed in claim 1 wherein the humectant is glycerine.

5. A formulation as claimed in claim 1 wherein the anti-inflammatory drugs are selected from Beta methasone valerate present in the range of 0.03 to 0.09 wt. %, Clobetasone propionate present in the range of 0.03 to 0.08 wt. %, Salicylic acid present in the range of 1 to 3 wt. % and Sandal wood oil in the range of 0.3 to 0.8 wt. %.

6. An herbal formulation as claimed in claim 1 wherein the *Gum olibanum* resinoid organic solvent extract is a *Gum olibanum* hexane extract.

7. An herbal formulation as claimed in claim 1 wherein the *Gum olibanum* resinoid organic solvent extract is a *Gum olibanum* methanolic extract.

8. A formulation as claimed in claim 1 wherein the base is a gel containing propylene gylcol, an acrylic polymer, and monoethanalamine.

9. An herbal formulation as claimed in claim 1 wherein the base is an aqueous cream containing an emulsifying ointment.

10. An herbal formulation as claimed in claim 1 wherein the skin disorders are selected from the group-consisting of Eczema and corns.

11. An herbal formulation as claimed in claim 1 wherein the formulation is used as an anti-inflammatory agent and wound healing agent.

12. An herbal formulation as claimed in claim 1 which is in the form of an emulsion of cream for application to the skin.

13. An herbal formulation as claimed in claim 1 wherein the plant extracts are obtained: from plant parts selected from leaf, root, bark, exudation of the bark, flowers, fruits, stem, or branch.

14. An herbal formulation as claimed in claim 1 wherein the formulation is used for alleviating muscular pain due to exertion.

15. A method for the treatment of Eczema comprising the steps of topically applying the herbal formulation as claimed in claim 1 at least two times a day for a period of 90–120 days.

16. A method for the treatment of corns on the toes comprising the steps of topically applying the herbal formulation as claimed in claim 1 at least two times a day for a period of 60–90 days.

17. A method for the treatment of muscular pain due to exertion comprising the steps of topically applying the herbal formulation as claimed in claim 1 at least two times a day for a period of at least two days.

* * * * *

UNITED STATES PATENT AND TRADEMARK OFFICE
CERTIFICATE OF CORRECTION

PATENT NO. : 6,383,495 B1
DATED : May 7, 2002
INVENTOR(S) : Ramakrishna et al.

It is certified that error appears in the above-identified patent and that said Letters Patent is hereby corrected as shown below:

Column 1,
Line 39, delete "It:" and insert -- It --.
Line 56, delete "use:" and insert -- use --.

Column 2,
Line 43, delete "olibanuim" and insert -- olibanum --.

Column 3,
Line 7, delete "mondethano" and insert -- menoethanol --.
Line 12, delete "erecia" and insert -- erecta --.

Column 4,
Line 11, delete "in," and insert -- in --.
Line 59, delete "C." and insert -- C --.

Column 9,
Line 1, delete "Olibqum" and insert -- Olibanum --.

Column 10,
Line 46, delete "Cldbetasone" and insert -- Clobetasone --.

Signed and Sealed this

Twenty-third Day of July, 2002

Attest:

JAMES E. ROGAN
Attesting Officer
Director of the United States Patent and Trademark Office